(12) United States Patent
McCarthy et al.

(10) Patent No.: US 9,554,787 B2
(45) Date of Patent: Jan. 31, 2017

(54) DEVICES AND METHODS FOR PERCUTANEOUS ACCESS, HEMOSTASIS, AND CLOSURE

(71) Applicant: Northwestern University, Evanston, IL (US)

(72) Inventors: Patrick M. McCarthy, Chicago, IL (US); Swaminadhan Gnanashanmugam, Evanston, IL (US); Usha Periyanayagam, Chicago, IL (US); Ingrid Lin, Eight Mile Plains (AU); Leah Ralph, Evanston, IL (US); Christopher Lubeck, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/499,822

(22) Filed: Sep. 29, 2014

(65) Prior Publication Data

US 2015/0087916 A1    Mar. 26, 2015

Related U.S. Application Data

(63) Continuation of application No. 12/922,306, filed as application No. PCT/US2009/037425 on Mar. 17, 2009, now abandoned.

(60) Provisional application No. 61/037,255, filed on Mar. 17, 2008.

(51) Int. Cl.
*A61B 17/00* (2006.01)
*A61B 17/02* (2006.01)
*A61B 17/34* (2006.01)

(52) U.S. Cl.
CPC ....... *A61B 17/0057* (2013.01); *A61B 17/0218* (2013.01); *A61B 17/3421* (2013.01); *A61B 17/3423* (2013.01); *A61B 2017/00243* (2013.01); *A61B 2017/00252* (2013.01); *A61B 2017/00575* (2013.01); *A61B 2017/00606* (2013.01); *A61B 2017/00867* (2013.01); *A61B 2017/0237* (2013.01); *A61B 2017/3425* (2013.01);

(Continued)

(58) Field of Classification Search
CPC ............ A61B 17/0057; A61B 17/3423; A61B 17/3431; A61B 2017/00575; A61B 2017/00592; A61B 2017/00597; A61B 2017/00606; A61B 2017/00646; A61B 2017/00676; A61B 2017/3425
See application file for complete search history.

(56) References Cited

U.S. PATENT DOCUMENTS

| 4,991,602 A | 2/1991 | Amplatz et al. |
| 5,067,489 A | 11/1991 | Lind |
| 5,366,478 A | 11/1994 | Brinkerhoff et al. |

(Continued)

FOREIGN PATENT DOCUMENTS

WO    9311716    6/1993

OTHER PUBLICATIONS

International Search Report and Written Opinion for PCT/US2009/037425, mailed Oct. 1, 2009, 11 pages.

*Primary Examiner* — Todd J Scherbel
(74) *Attorney, Agent, or Firm* — Casimir Jones SC; David W. Staple

(57) ABSTRACT

The present invention provides methods and devices for obtaining percutaneous access, maintaining hemostasis, and providing closure of openings in tissues of the body. In particular, the present invention provides methods and devices for maintaining hemostasis and providing closure surgical incisions of the left ventricular apex of the heart.

9 Claims, 5 Drawing Sheets

(52) U.S. Cl.
CPC ............... *A61B 2017/3484* (2013.01); *A61B 2017/3488* (2013.01)

(56) References Cited

U.S. PATENT DOCUMENTS

| | | |
|---|---|---|
| 5,861,003 A | 1/1999 | Latson et al. |
| 7,011,095 B2 | 3/2006 | Wolf et al. |
| 8,029,522 B2 | 10/2011 | Ortiz et al. |
| 8,182,530 B2 | 5/2012 | Huber |
| 8,226,553 B2 | 7/2012 | Shelton et al. |
| 2005/0049634 A1 | 3/2005 | Chopra |
| 2005/0228434 A1 | 10/2005 | Amplatz et al. |
| 2005/0288706 A1 | 12/2005 | Widomski et al. |
| 2006/0149306 A1 | 7/2006 | Hart et al. |
| 2007/0073337 A1 | 3/2007 | Abbott et al. |
| 2007/0118021 A1 | 5/2007 | Pokorney |
| 2009/0143713 A1 | 6/2009 | Van Dam et al. |
| 2009/0312789 A1 | 12/2009 | Kassab et al. |
| 2011/0040324 A1 | 2/2011 | McCarthy et al. |

A

A

B

C

D

E

DEVICES AND METHODS FOR PERCUTANEOUS ACCESS, HEMOSTASIS, AND CLOSURE

The present application is a continuation of U.S. patent application Ser. No. 12/922,306, filed Oct. 19, 2010, which is a §371 U.S. National Entry of International Patent Application PCT/US2009/037425, filed Mar. 17, 2009, which claims priority to U.S. Provisional Patent Application Ser. No. 61/037,255 filed Mar. 17, 2008, each of which are herein incorporated by reference in their entireties.

FIELD OF THE INVENTION

The present invention provides methods and devices for obtaining percutaneous access, maintaining hemostasis, and providing closure of openings in tissues of the body. In particular, the present invention provides methods and devices for maintaining hemostasis and providing closure surgical incisions of the left ventricular apex of the heart.

BACKGROUND OF THE INVENTION

Historically, human heart valves have been replaced using open heart surgery involving the heart/lung machine and excision of the native aortic valve and suture placement of the new valve prosthesis. New technology has been developed to enable valve replacement "percutaneously," or through a "transapical" procedure, using a device with a valve inside a stent placed within the patient's native aortic valve. Percutaneous valve procedures pertain to making small incisions in the skin to allow direct access to peripheral vessels or body channels to insert catheters. Transapical valve procedures pertain to making a small incision in or near the apex of a heart to allow valve access. Transapical procedures present an advance in cardiac care as they provide faster patient recovery, shorter procedure time, and larger addressable patient population without the need for sternotomy or cardiopulmonary bypass. These procedures still require hemostasis and pacing during the procedure and generally utilize sutures for closure. The distinction between percutaneous valve procedures and minimally invasive procedures is also highlighted in a recent position statement of the Society of Thoracic Surgeons (STS), the American Association for Thoracic Surgery (AATS), and the Society for Cardiovascular Angiography and Interventions (SCAI; Vassiliades Jr. T A, Block P C, Cohn L H, Adams D H, Borer J S, Feldman T, Holmes D R, Laskey W K, Lytle B W, Mack M F, Williams D O. The clinical development of percutaneous heart valve technology: a position statement by the Society of Thoracic Surgeons (STS), the American Association for Thoracic Surgery (AATS), and the Society for Cardiovascular Angiography and Interventions (SCAI). J Thorac Cardiovasc Surg. 2005; 129:970-6). Because minimally invasive approaches require smaller incisions, they generally allow for faster patient recovery with less pain and bodily trauma. This, in turn, reduces the medical costs and the overall disruption to the life of the patient. The use of minimally invasive approaches, however, introduces new complexities to surgery. An inherent difficulty in the minimally invasive percutaneous approach is the limited space that is available within the vasculature. Unlike open heart surgery, percutaneous heart surgery offers a surgical field that is only as large as the diameter of the blood vessel used for access. Consequently, the introduction of tools and prosthetic devices becomes a great deal more complicated as compared to open-chest surgeries. The device must be dimensioned and configured to permit it to be introduced into the vasculature, maneuvered therethrough, and positioned at a desired location. This may involve passage through significant convolutions, at some distance from the initial point of introduction, before placement can be made at the intended site. The existing technology is still in an early phase of development, as is the procedure for placement of these devices. One route of access, through the femoral arteries, is limited because of vascular disease involving these vessels and the size of the devices to be placed is largely relative to the small diameter vessels. Transapical placement, through the apex of the left ventricle, has been the preferred approach in many patients because there are less vascular complications, but there are problems such as bleeding from the left ventricular apex requiring difficult suture closure, and a thoracotomy incision that can be painful and lead to difficult recovery and prolonged hospital stay for the patient. What is needed are improved devices and methods for carrying out minimally invasive procedures.

SUMMARY

In some embodiments, the present invention provides a medical closure device comprising one or more elements (e.g. cylinder elements), a proximal expanded element and a distal expanded element, wherein the distal expanded element is configured to adopt a reduced profile configuration upon inserting the distal expanded element into a confined space, wherein the distal expanded element is configured to readopt a high profile configuration upon exit from a confined space, and wherein the medical closure device comprises one or more impermeable surfaces configured to occlude blood flow through an opening in a body tissue. The element may be of any suitable shape. Many of the embodiments described below are illustrated using cylinder elements, but the devices are not limited to such configurations, unless otherwise specified. In some embodiments, the body tissue comprises the left ventricular apex. In some embodiments, an opening comprises a surgical incision. In some embodiments, the medical closure device is configured for insertion into an opening in a body tissue. In some embodiments, insertion is assisted by a delivery device. In some embodiments, one or more cylinder elements comprise inner lumens. In some embodiments, the medical closure device comprises or consists of one cylinder element. In some embodiments, the medical closure device comprises a proximal cylinder element and a distal cylinder element. In some embodiments, the distal cylinder element is configured to fit axially within the inner lumen of the proximal cylinder element. In some embodiments, the distal cylinder element is configured to lock in place within the proximal cylinder element. In some embodiments, one or more of the inner lumens comprise a one-way valve. In some embodiments, a one-way valve is configured to occlude the flow of blood through one or more inner lumens. In some embodiments, a one-way valve is configured to provide access to medical instruments from the proximal end of the medical closure device to the distal end of the medical closure device through one or more inner lumens. In some embodiments, the medical closure device comprises a metal fabric skeleton. In some embodiments, the metal fabric skeleton comprises one or more shape memory materials. In some embodiments, the medical closure device comprises a blood-impermeable skin. In some embodiments, the blood-impermeable skin comprises a polymer coating.

In some embodiments, the present invention provides a medical closure device comprising (a) a proximal unit, wherein the proximal unit comprises a proximal cylinder and a proximal expanded element; and (b) a distal unit, wherein the distal unit comprises a distal cylinder and a distal expanded element; wherein the proximal cylinder and the distal cylinder comprise inner lumens; wherein one or more of the inner lumens comprise a one-way valve; wherein the proximal cylinder is configured to attach to the distal cylinder; wherein the distal expanded element is configured to adopt a reduced profile configuration upon inserting the distal expanded element into a confined space; wherein the distal expanded element is configured to readopt a high profile configuration upon exit from a confined space; wherein the medical closure device is configured to be inserted into a surgical incision in a body tissue; and wherein the medical closure device comprises one or more impermeable surfaces configured to occlude blood flow.

In some embodiments, the present invention provides a medical closure device comprising a single unit comprising cylinder element, a proximal expanded element and a distal expanded element; wherein the cylinder element comprises an axial aperture; wherein the axial aperture comprises a one-way valve; wherein the proximal expanded element and the distal expanded element comprise a shape memory material; wherein the proximal expanded element and the distal expanded element are configured to adopt a reduced profile configuration under applied pressure, wherein the proximal expanded element and the distal expanded element are configured to readopt a high profile configuration upon release of applied pressure, wherein the medical closure device is configured to be deployed into an opening in a body tissue, and wherein the medical closure device comprises one or more impermeable surfaces configured to occlude blood flow.

In some embodiments, the present invention provides a medical closure device comprising a single unit comprising: a cylinder element, a proximal expanded element and a distal expanded element, wherein the distal expanded element is configured to adopt a reduced profile configuration under applied pressure, and wherein the medical closure device comprises one or more impermeable surfaces configured to occlude blood flow. In some embodiments, the medical closure device is configured to create an occlusion within an opening a in body tissue. In some embodiments, the body tissue comprises coronary tissue. In some embodiments, the coronary tissue comprises the left ventricular apex. In some embodiments, the opening comprises a surgical incision. In some embodiments, the medical closure device is configured for insertion into an opening. In some embodiments, the insertion is assisted by a delivery device. In some embodiments, the delivery device comprises a catheter. In some embodiments, the medical closure device comprises one or more shape memory materials. In some embodiments, the medical closure device comprises a metal fabric. In some embodiments, the metal fabric comprises NiTi. In some embodiments, the medical closure device comprises a blood-impermeable skin. In some embodiments, the blood-impermeable skin comprises a polymer coating. In some embodiments, the cylinder element comprises an inner lumen. In some embodiments, the inner lumen comprises a valve. In some embodiments, the valve is configured to limit the flow of blood through the inner lumen. In some embodiments, the valve is configured to occlude the flow of blood through the inner lumen. In some embodiments, the valve comprises a one-way valve. In some embodiments, the one-way valve is configured to limit the flow of blood from the distal end of the medical closure device to the proximal end of the medical closure device through the inner lumen. In some embodiments, the one-way valve is configured to provide access from the proximal end of the medical closure device to the distal end of the medical closure device through the inner lumen. In some embodiments, access comprises inserting medical instruments through the inner lumen. In some embodiments, the distal expanded element is configured to adopt a reduced profile configuration from pressure applied by inserting the distal expanded element into a confined space. In some embodiments, a confined space comprises a catheter. In some embodiments, a confined space comprises an opening in a body tissue. In some embodiments, an opening in a body tissue comprises a surgical incision. In some embodiments, the distal expanded element is configured to readopt a high profile configuration upon exit from a confined space. In some embodiments, the distal expanded element is configured to readopt a high profile configuration upon release of applied pressure. In some embodiments, the proximal end of the cylinder element comprises threading. In some embodiments, the distal end of the cylinder element comprises threading. In some embodiments, the proximal and distal ends of the cylinder element comprise threading.

In some embodiments, the present invention provides a medical closure device comprising (a) a proximal unit, wherein the proximal unit comprises a proximal cylinder and a proximal expanded element, and (b) a distal unit, wherein the distal unit comprises a distal cylinder and a proximal expanded element; wherein the proximal cylinder is configured to attach to the distal cylinder; wherein the distal expanded element is configured to adopt a reduced profile configuration under applied pressure, and wherein the medical closure device comprises one or more impermeable surfaces configured to occlude blood flow. In some embodiments, the medical closure device is configured to create an occlusion within an opening a in body tissue. In some embodiments, the body tissue comprises coronary tissue. In some embodiments, the coronary tissue comprises the left ventricular apex. In some embodiments, the opening comprises a surgical incision. In some embodiments, the medical closure device is configured for insertion into an opening. In some embodiments, the insertion is assisted by a delivery device. In some embodiments, a delivery device comprises a catheter. In some embodiments, the medical closure device comprises one or more shape memory materials. In some embodiments, the medical closure device comprises a metal fabric. In some embodiments, a metal fabric comprises NiTi. In some embodiments, the medical closure device comprises a blood-impermeable skin. In some embodiments, a blood-impermeable skin comprises a polymer coating. In some embodiments, the proximal cylinder element and the distal cylinder elements comprise inner lumens. In some embodiments, the distal cylinder element is configured to fit within the inner lumen of the proximal cylinder element. In some embodiments, the distal cylinder element is configured to lock in place within the proximal cylinder element. In some embodiments, the inner lumen of the distal cylinder comprises a valve. In some embodiments, the valve is configured to limit the flow of blood through the inner lumen. In some embodiments, the valve is configured to occlude the flow of blood through the inner lumen. In some embodiments, the valve comprises a one-way valve. In some embodiments, the one-way valve is configured to limit the flow of blood from the distal end of the medical closure device to the proximal end of the medical closure device through the inner lumens. In some embodiments, the one-way valve is configured to provide access from the proximal end of the medical closure device to the distal end of the medical closure device through the inner lumens. In some embodiments, access comprises inserting medical instruments through the one-way valve and the inner lumens. In some embodiments, the distal expanded element is configured to adopt a reduced profile configuration from pressure applied by inserting the distal expanded element into a confined space. In some embodiments, the confined space comprises a catheter. In some embodiments, the confined space comprises an opening in a body tissue. In some embodiments, an opening in a body tissue comprises a surgical incision. In some embodiments, the distal expanded element is configured to readopt a high profile configuration upon exit from a confined space. In some embodiments, the distal expanded element is configured to readopt a high profile configuration upon release of applied pressure. In some embodiments, the proximal end of the proximal cylinder element comprises threading. In some embodiments, the distal end of the distal cylinder element comprises threading.

BRIEF DESCRIPTION OF THE DRAWINGS

The foregoing summary and detailed description is better understood when read in conjunction with the accompanying drawings which are included by way of example and not by way of limitation.

DETAILED DESCRIPTION OF EMBODIMENTS

The present invention provides methods and devices for obtaining access to chambers of the heart (e.g. left ventricular apex), maintaining hemostasis, and closing the chamber (e.g. left ventricular apex) through, for example, a percutaneous or minimally invasive approach to enable a variety of intra-cardiac procedures. While embodiments of the invention are illustrated using intra-cardiac procedures, it will be understood that the devices find use in a variety of other medical application as well. In some embodiments, the present invention would find use in the placement of percutaneous valve technology (e.g. percutaneous aortic valve replacement). In some embodiments, the present invention finds use in percutaneous mitral valve technology, percutaneous ablation for heart rhythm abnormalities (e.g. atrial fibrillation, ventricular tachycardia, etc.), placement of a ventricular "partitioning" device to improve cardiac function in patients with prior myocardial infarction, and other intra-cardiac procedures.

Figure 2:
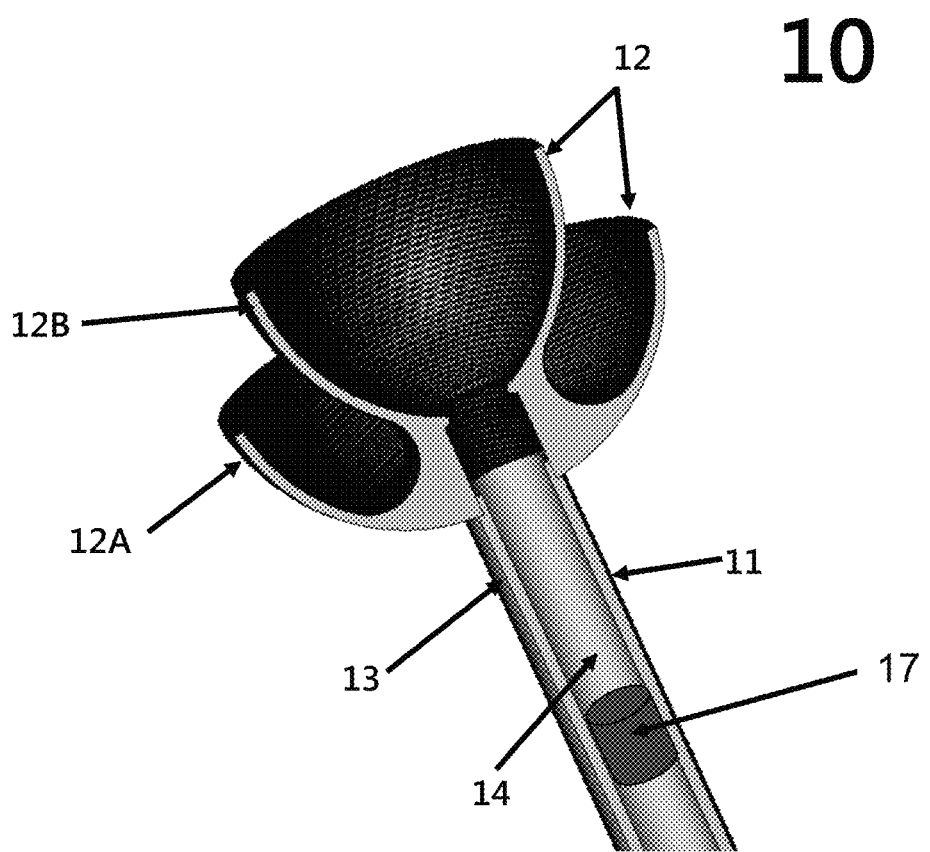
FIG. 2 shows schematics of a medical device of some embodiments of the present invention.
Figure 3:
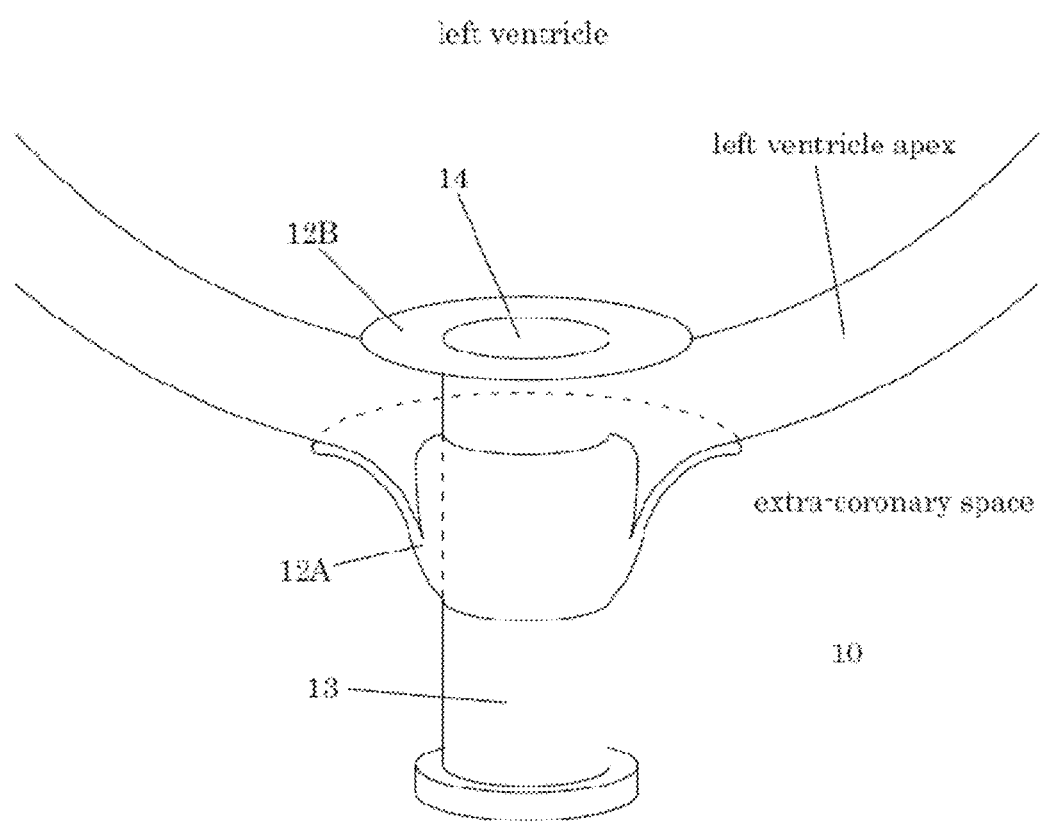
FIG. 3 shows a schematic of a medical device of some embodiments of the present invention deployed on a left ventricular apex.

In some embodiments, a device of the present invention comprises one or more component parts. In some embodiments, the present invention comprises a single unit 10 (SEE FIGS. 1A and 2). In some embodiments, the present invention comprises a cylinder element 11. In some embodiments, a plurality of expanded elements 12 extends from the cylinder element 11 (e.g. two expanded elements). In some embodiments, the present invention comprises a proximal expanded element 12A and a distal expanded element 12B. In some embodiments, the expanded elements 12 are of different sizes. In some embodiments, the distal expanded element 12B is smaller in circumference that the proximal expanded element 12A. In some embodiments, the distal expanded element 12B is deformable to a lesser cross-sectional dimension. In some embodiments, the distal expanded element 12B is deformable to a lesser cross-sectional profile to accommodate insertion of the proximal end of the cylinder element 11 and distal expanded element 12B through a channel in the tissue of a subject. In some embodiments, the proximal expanded element 12A is deformable to a lesser cross-sectional dimension. In some embodiments, the proximal expanded element 12A and a distal expanded element 12B are configured to sit on either side of a tissue of a subject when the cylinder element 11 is inserted through a channel in the tissue of a subject (SEE FIG. 3). In some embodiments, the cylinder element 11 comprises a cylinder unit outer surface 13 configured for optimal interaction with device placement environment (e.g. coronary tissue and chambers). In some embodiments, the cylinder element 11 comprises an inner lumen 14. In some embodiments, the cylinder element 11 is fitted with proximal threads 15 and distal threads 16 configured for attachment to additional systems or devices (e.g. tubing, cap, plug, occlusion device, etc.).

Figure 1:
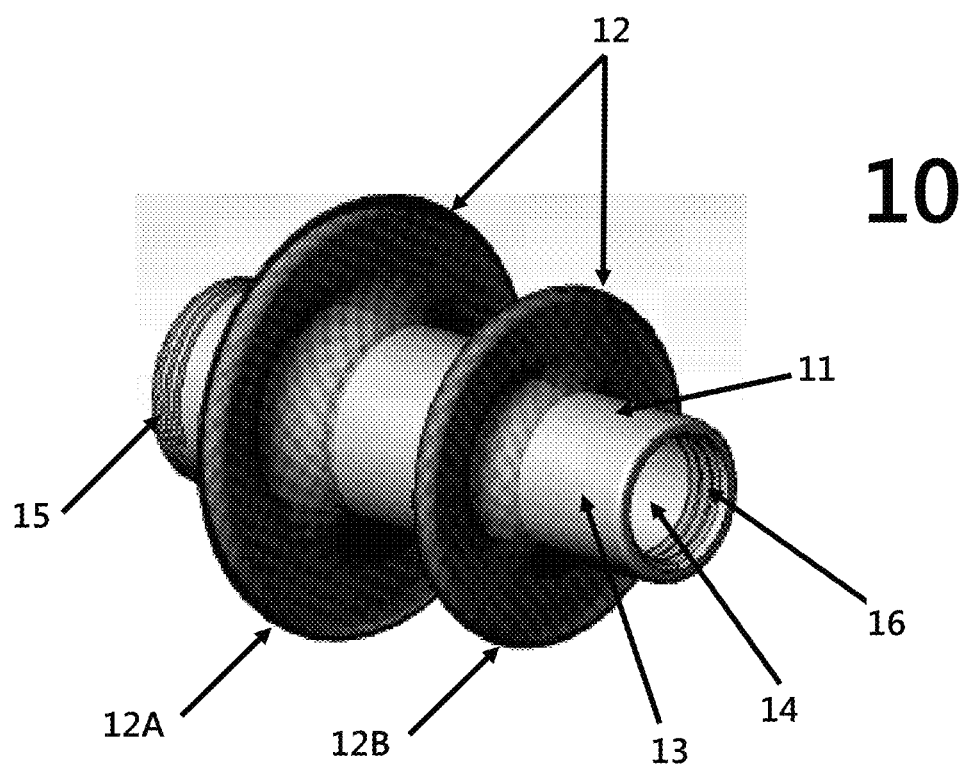
FIGS. 1A and 1B show schematics of a medical device of some embodiments of the present invention; (A) a single unit device of assembled multi unit device, (B) a disassembled two-subunit device.
Figure 1:
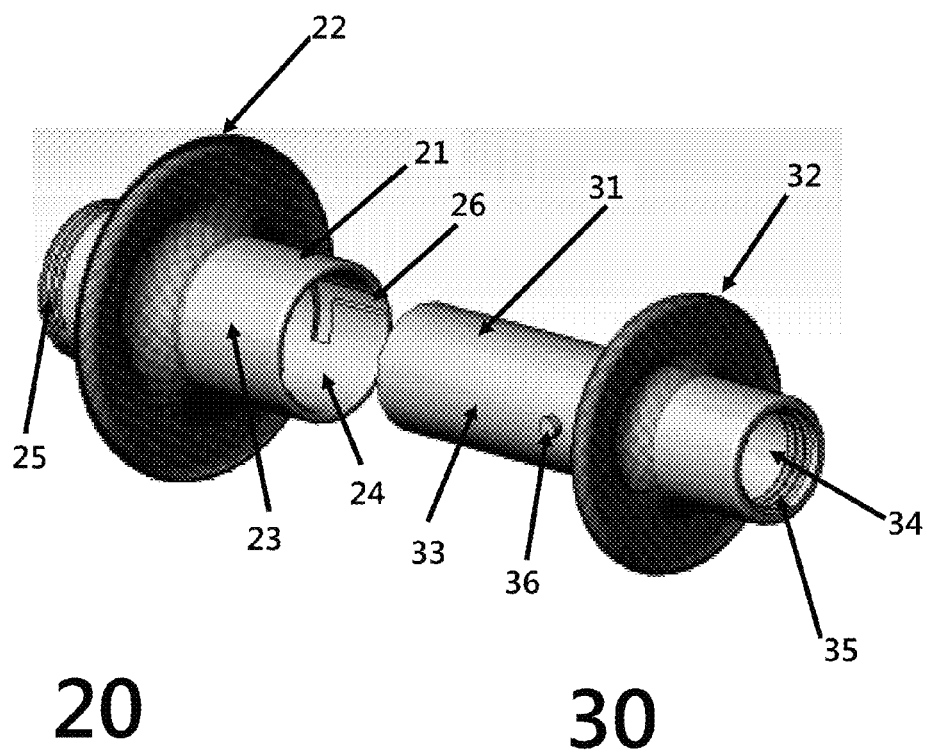

In some embodiments, the present invention comprises two connectable units (SEE FIG. 1B). In some embodiments, the present invention comprises a proximal unit 20 and a distal unit 30. In some embodiments, the proximal unit 20 comprises a proximal cylinder 21 and a proximal expanded element 22. In some embodiments, the proximal cylinder 21 comprises a proximal cylinder outer surface 23 configured for optimal interaction with a device placement environment (e.g. coronary tissue and chambers). In some embodiments, the proximal cylinder 21 comprises a proximal inner lumen 24. In some embodiments, the proximal unit 20 comprises proximal threading 25. In some embodiments, the proximal unit 20 comprises proximal threading 25 at the most proximal end of the proximal unit 20. In some embodiments, the proximal unit 20 comprises an inter-unit connector 26. In some embodiments, the proximal unit 20 comprises an inter-unit connector 26 at the distal end of the proximal unit 20. In some embodiments, the distal unit 30 comprises a distal cylinder 31 and a distal expanded element 32. In some embodiments, the distal cylinder 31 comprises a distal cylinder outer surface 33 configured for optimal interaction with a device placement environment (e.g. coronary tissue and chambers). In some embodiments, the distal cylinder 31 comprises a distal inner lumen 34. In some embodiments, the distal unit 30 comprises distal threading 35. In some embodiments, the distal unit 30 comprises distal threading 35 at the most distal end of the distal unit 30. In some embodiments, the distal unit 30 comprises an inter-unit connector 36. In some embodiments, the distal unit 30 comprises an inter-unit connector 36 at the proximal end of the distal unit 30.

In some embodiments, the distal cylinder 31 of the distal unit 30 is smaller in circumference than the proximal cylinder 21 of the proximal unit 20. In some embodiments, the distal cylinder outer surface 33 of the distal unit is configured to fit snugly within the proximal inner lumen 24 of the proximal unit 20. In some embodiments, the inter-unit connector 36 at the proximal end of the distal unit 30 is located on the outside of the distal cylinder outer surface 33. In some embodiments, the inter-unit connector 26 at the distal end of the proximal unit 20 is located within the proximal inner lumen 24 of the proximal unit 20. In some embodiments, the distal cylinder outer surface 33 of the distal unit 30 is configured to slidably engage the proximal inner lumen 24 of the proximal unit 20 bringing the inter-unit connector 36 at the proximal end of the distal unit 30 into contact with the inter-unit connector 26 at the distal end of the proximal unit 20. In some embodiments, contact and engagement of the inter-unit connector 36 of the distal unit 30 with the inter-unit connector 26 of the proximal unit 20 locks the distal cylinder 31 of the distal unit 30 within the proximal cylinder 21 of the proximal unit 20, thus locking the distal unit and proximal unit together in one single unit 10 (SEE FIGS. 1A and 1B). In some embodiments, the engaged distal cylinder 31 and proximal cylinder 21 form a single cylinder element 11. In some embodiments, the connected elements of the proximal unit 20 and distal unit 30 functionally and/or structurally correlate to elements of a single unit 10, when connected. In some embodiments, an inter-unit connector 36 of the distal unit 30 and a inter-unit connector 26 of the proximal unit 20 function through any suitable locking and/or interaction mechanism, including but not limited to bayonet-style attachment, lock-and-key, threading, etc.

In some embodiments, the proximal cylinder 21 of the proximal unit 20 is smaller in circumference than the distal cylinder 31 of the distal unit 30. In some embodiments, the proximal cylinder outer surface 23 of the proximal unit 20 is configured to fit snugly within the distal inner lumen 34 of the distal unit 30. In some embodiments, the inter-unit connector 26 at the distal end of the proximal unit 20 is located on the outside of the proximal cylinder outer surface 23. In some embodiments, the inter-unit connector 36 at the proximal end of the distal unit 30 is located within the distal inner lumen 34 of the distal unit 30. In some embodiments, the proximal cylinder outer surface 23 of the proximal unit 20 is configured slidably engage the distal inner lumen 34 of the distal unit 30 bringing the inter-unit connector 26 at the distal end of the proximal unit 20 into contact with the inter-unit connector 36 at the proximal end of the distal unit 30. In some embodiments, contact and engagement of the inter-unit connector 26 of the proximal unit 20 with the inter-unit connector 36 of the distal unit 30 locks the proximal cylinder 21 of the proximal unit 20 within the distal cylinder 31 of the distal unit 30, thus locking the distal unit and proximal unit together in one single unit 10. In some embodiments, the engaged distal cylinder 31 and proximal cylinder 21 form a single cylinder element 11. In some embodiments, the connected elements of the proximal unit 20 and distal unit 30 functionally and/or structurally correlate to elements of a single unit 10, when connected.

In some embodiments, the cylinder element 11, distal cylinder 31, and/or proximal cylinder 21 has an outer diameter of at least 1 mm (e.g. >1 mm, >2 mm, >3 mm, >4 mm, >5 mm, >6 mm, >7 mm, >8 mm, >9 mm, >1 cm, >1.1 cm, >1.2 cm, >1.3 cm, >1.4 cm, >1.5 cm, >1.6 cm, >1.7 cm, >1.8 cm, >1.9 cm, >2 cm, >2.1 cm, >2.2 cm, >2.3 cm, >2.4 cm, >2.5 cm, >2.6 cm, >2.7 cm, >2.8 cm, >2.9 cm, etc.). In some embodiments, the cylinder element 11, distal cylinder 31, and/or proximal cylinder 21 has an outer diameter of less than 3 cm (e.g. <3 cm, <2.9 cm, <2.8 cm, <2.7 cm, <2.6 cm, <2.5 cm, <2.4 cm, <2.3 cm, <2.2 cm, <2.1 cm, <2 cm, <1.9 cm, <1.8 cm, <1.7 cm, <1.6 cm, <1.5 cm, <1.4 cm, <1.3 cm, <1.2 cm, <1.1 cm, <1 cm, <9 mm, <8 mm, <7 mm, <6 mm, <5 mm, <4 mm, <3 mm, <2 mm, <1 mm, etc.).

In some embodiments, an expanded element 12, distal expanded element 12B, proximal expanded element 12A, proximal expanded element 22, and/or distal expanded element 32 may be of any suitable shape including by not limited to curved, symmetrical, bowed, rounded, oblong, oval, straight, angled, obtuse, asymmetrical, spiraled, spherical, circular, derivatives thereof, combinations thereof, etc. In some embodiments, an expanded element 12, distal expanded element 12B, proximal expanded element 12A, proximal expanded element 22, and/or distal expanded element 32 may be curved.

In some embodiments, an expanded element 12, distal expanded element 12B, proximal expanded element 12A, proximal expanded element 22, and/or distal expanded element 32 has a maximum expanded outer diameter of greater than 2 mm (e.g. >2 mm, >3 mm, >4 mm, >5 mm, >6 mm, >7 mm, >8 mm, >9 mm, >1 cm, >1.1 cm, >1.2 cm, >1.3 cm, >1.4 cm, >1.5 cm, >1.6 cm, >1.7 cm, >1.8 cm, >1.9 cm, >2 cm, >2.1 cm, >2.2 cm, >2.3 cm, >2.4 cm, >2.5 cm, >2.6 cm, >2.7 cm, >2.8 cm, >2.9 cm, >3 cm, >3.1 cm, >3.2 cm, >3.3 cm, >3.4 cm, >3.5 cm, >3.6 cm, >3.7 cm, >3.8 cm, >3.9 cm, >4 cm, >4.1 cm, >4.2 cm, >4.3 cm, >4.4 cm, >4.5 cm, >4.6 cm, >4.7 cm, >4.8 cm, >4.9 cm, >5 cm, >5.1 cm, >5.2 cm, >5.3 cm, >5.4 cm, >5.5 cm, >5.6 cm, >5.7 cm, >5.8 cm, >5.9 cm, >6 cm, >6.1 cm, >6.2 cm, >6.3 cm, >6.4 cm, >6.5 cm, >6.6 cm, >6.7 cm, >6.8 cm, >6.9 cm, >7 cm, >7.1 cm, >7.2 cm, >7.3 cm, >7.4 cm, >7.5 cm, >7.6 cm, >7.7 cm, >7.8 cm, >7.9 cm, etc.). In some embodiments, a expanded element 12, distal expanded element 12B, proximal expanded element 12A, proximal expanded element 22, and/or distal expanded element 32 has a maximum expanded outer diameter of less than 10 cm (e.g. <10 cm, <9 cm, <8 cm, <7 cm, <6 cm, <5 cm, <4.9 cm, <4.8 cm, <4.7 cm, <4.6 cm, <4.5 cm, <4.4 cm, <4.3 cm, <4.2 cm, <4.1 cm, <4 cm, <3.9 cm, <3.8 cm, <3.7 cm, <3.6 cm, <3.5 cm, <3.4 cm, <3.3 cm, <3.2 cm, <3.1 cm, <3 cm, <2.9 cm, <2.8 cm, <2.7 cm, <2.6 cm, <2.5 cm, <2.4 cm, <2.3 cm, <2.2 cm, <2.1 cm, <2 cm, <1.9 cm, <1.8 cm, <1.7 cm, <1.6 cm, <1.5 cm, <1.4 cm, <1.3 cm, <1.2 cm, <1.1 cm, <1 cm, etc.).

In some embodiments, an expanded element 12, distal expanded element 12B, proximal expanded element 12A, proximal expanded element 22, and/or distal expanded element 32 of the present invention is deformable such that the outer diameter is decreased. In some embodiments, a decrease in outer diameter of a expanded element 12, distal expanded element 12B, proximal expanded element 12A, proximal expanded element 22, and/or distal expanded element 32 of the present invention is configured to be deformed to a decreased outer diameter when sliding through an opening or channel (e.g. surgical incision) in a tissue of a subject. In some embodiments, a expanded element 12, distal expanded element 12B, proximal expanded element 12A, proximal expanded element 22, and/or distal expanded element 32 of the present invention is configured to be deformed to a decreased outer diameter of less than 3 cm (e.g. <3 cm, <2.9 cm, <2.8 cm, <2.7 cm, <2.6 cm, <2.5 cm, <2.4 cm, <2.3 cm, <2.2 cm, <2.1 cm, <2 cm, <1.9 cm, <1.8 cm, <1.7 cm, <1.6 cm, <1.5 cm, <1.4 cm, <1.3 cm, <1.2 cm, <1.1 cm, <1 cm, <9 mm, <8 mm, <7 mm, <6 mm, <5 mm, <4 mm, etc.). In some embodiments, a expanded element 12, distal expanded element 12B, proximal expanded element 12A, proximal expanded element 22, and/or distal expanded element 32 of the present invention is configured to be deformed to a decreased outer diameter greater than 2 mm (e.g. >2 mm, >3 mm, >4 mm, >5 mm, >6 mm, >7 mm, >8 mm, >9 mm, >1 cm, >1.1 cm, >1.2 cm, >1.3 cm, >1.4 cm, >1.5 cm, >1.6 cm, >1.7 cm, >1.8 cm, >1.9 cm, >2 cm, >2.1 cm, >2.2 cm, >2.3 cm, >2.4 cm, >2.5 cm, >2.6 cm, >2.7 cm, >2.8 cm, >2.9 cm, etc.).

In some embodiments, elements of the present invention are deformable (e.g. adopt a reduced-profile configuration) under defined amounts of pressure. In some embodiments, an expanded element 12, distal expanded element 12B, proximal expanded element 12A, proximal expanded element 22, and/or distal expanded element 32 of the present invention is deformable (e.g. reduce cross-sectional profile) under pressure (e.g. pressure applied when a device is inserted into a channel (e.g. surgical incision) in a tissue (e.g. coronary wall), pressure applied when a device is inserted into a delivery device, etc.). In some embodiments, an expanded element 12, distal expanded element 12B, proximal expanded element 12A, proximal expanded element 22, and/or distal expanded element 32 of the present invention may be of any suitable rigidity, elastic modulus, elasticity, stiffness, compliance, rotational stiffness, and/or deformability. In some embodiments, a suitable rigidity, elastic modulus, elasticity, stiffness, compliance, rotational stiffness, and/or deformability for a expanded element 12, distal expanded element 12B, proximal expanded element 12A, proximal expanded element 22, and/or distal expanded element 32 of the present invention is selected based on any of the following criteria: ability to deform to a smaller outer diameter under a defined pressure, ability to withstand deformation under a defined pressure, ability to conform to a selected shape under a selected pressure, ability to maintain shape, ability to offer resistance to a defined pressure, ability to deform under defined boundary conditions, ability to withstand deformation under defined boundary conditions, etc. In some embodiments, the material, conformation, thickness, size, width, curvature, diameter, and/or other dimensions and factors of a expanded element 12, distal expanded element 12B, proximal expanded element 12A, proximal expanded element 22, and/or distal expanded element 32 of the present invention are selected to provide characteristics (e.g rigidity, elastic modulus, elasticity, stiffness, compliance, rotational stiffness, deformability, etc.) desired for a selected application.

In some embodiments, the present invention provides a device which engages a tissue of a subject (e.g. coronary wall). In some embodiments, the cylinder element 11 is inserted though a channel (e.g. surgical incision) in a tissue (e.g. coronary wall). In some embodiments, inserting of the cylinder element 11 through the tissue results in placement of the distal expanded element 12B and proximal expanded element 12A on opposing sides of the tissue through which the cylinder element 11 is inserted. In some embodiments, insertion of the device into the channel in the tissue requires a deformation of the distal expanded element 12B to reduce the cross-sectional profile of the distal expanded element 12B. In some embodiments, the distal expanded element 12B and proximal expanded element 12A fit firmly against the tissue (e.g. coronary wall) to create a seal around the channel (e.g. surgical incision). In some embodiments, the distal expanded element 12B resides on one side (e.g. left ventricle) of a tissue (e.g. coronary wall (e.g. left ventricle apex)) while the proximal expanded element 12A resides on the other side (e.g. outside surface of the heart) of the same tissue. In some embodiments, the inner lumen 14 of the cylinder element 11 provides a channel of defined size and shape through which medical procedures can be performed (e.g. passing of instruments, devices, wires, systems, agents, performing medical or surgical procedures, etc.). In some embodiments, the expanded elements 12 adopt the same orientation when deployed, whether the device is a single unit 10 or comprised of a distal unit 30 and proximal unit 20.

In some embodiments, a device of the present invention comprises a valve within the cylinder unit 11. In some embodiments, a device of the present invention provides a one-way valve. In some embodiments, a one-way valve is configured to allow procedural or surgical elements to enter the device from the proximal end. In some embodiments, a one-way valve is configured to impede, limit, or stop the flow of fluid (e.g. blood) into or through a device of the present invention. In some embodiments, a one-way valve is configured to regulate flow through the device. In some embodiments, a one-way valve is configured to impede, limit, or stop the flow of fluid (e.g. blood) into or through the device from the distal end. In some embodiments, the opening through the device (e.g. lumen, aperture, etc.) provides a hemostatic valve or other property in place to maintain hemostasis and pressurization (e.g. a one way valve, sealing device, etc.) so as to facilitate interventions through the lumen of this closure device, if necessary, either at the time of its initial deployment or anytime thereafter. In some embodiments, a device of the present invention functions as a sealable port to a blood-filled chamber of the body through which other devices can enter or exit (e.g. introducer sheath). In some embodiments, a device of the present invention provides a closure device. In some embodiments, the device itself provides closure. In some embodiments, added elements (e.g. cap, plug, occlusion, etc.) may be integrated into or onto a device of to close the lumen, occlude the lumen, seal the lumen or in other way change its property such that sealing and closure between a blood filled, likely pressurized compartment such as an artery or a heart chamber, and compartments such as the thoracic cavity, abdominal cavity, the leg or tissue or other areas, are closed off. In some embodiments of the closure device provides, in addition to, or in place of, the occlusion mechanisms above, a glue or similar type adhesive material which is used or eluted from the device to facilitate further bonding of the device to the tissue through which it is inserted to facilitate additional closure. For example, the elution of a fibrin glue or similar substance through the polymer embedded into the device through the outside of the device, in contact with the myocardial, endocardial or epicardial or all of those tissues, such that further adhesion and bonding can take place and help facilitate closure.

In some embodiments, a device is completely collapsible into a different configuration such as to facilitate a minimally invasive or percutaneous implantation. In some embodiments, a device is placed through an incision in the skin and then into the heart itself and then expanded into its full deployed position, which is likely to be larger in total diameter than the hole through which it is inserted into the skin and/or the hole through which it is inserted into the heart.

The methods and devices of the present invention provide improvements over existing technologies for placement of a percutaneous valve, and other intracardiac procedures. In some embodiments, the devices and methods remove the problems with femoral artery access, for example, by accessing the aortic valve through the left ventricular apex. In some embodiments, the devices and methods reduce the risk for peri-procedural stroke. In some embodiments, the devices and methods remove the problems with femoral artery access by accessing the aortic valve through the left ventricular apex and reduce the risk for peri-procedural stroke. The devices and methods obviate the need for a thoracotomy, leading to improved results (e.g. quicker patient recovery, reduced pain, reduced hospital length of stay), and quicker physician acceptance of this new procedure.

In some embodiments a device of the present invention provides, a nitinol mesh with a hemostatic component (e.g., expanded polytetrafluoroethylene (ePTFE)). In some embodiments, the outer surface of a device of the present invention is provided with a smooth coating to allow ease of movement (e.g. TEFLON, HDPE, nylon, PEBAX, PEEK, PTFE, a water-activated lubricant coating, or other suitable materials). In some embodiments, a device of the present invention comprises a metal fabric (e.g. NiTi). In some embodiments, a device of the present invention comprises a metal fabric (e.g. NiTi) coated or covered in a surface-forming material (e.g. polymer). In some embodiments, a metal fabric comprises a skeleton of a closure device and a surface material (e.g. polymer) comprises a skin over the skeleton. In some embodiments, a skin provides an impermeable (e.g. impermeable to blood) surface between pieces of a metal fabric skeleton. In some embodiments, a closure device is comprised of a shape memory material (e.g. shape memory alloy, shape/memory metal, smart metal, memory alloy, muscle wire, etc.), for example nitinol, chrome cobalt, copper-zinc-aluminum-nickel, copper-aluminium-nickel, and nickel-titanium (NiTi), etc. In some embodiments, a closure device is comprised of a single piece of shape memory material. In some embodiments, a closure device is comprised of any suitable metal or non-metal material (e.g. metals (e.g. Lithium, Magnesium, Aluminium, Titanium, Vanadium, Chromium, Manganese, Cobalt, Nickel, Copper, Zinc, Zirconium, Molybdenium, Silver, Cadmium, Antimony, Barium, Osmium, Platinum, Mercury, Thallium, Lead, etc.), plastics (e.g. Bakelite, neoprene, nylon, PVC, polystyrene, polyacrylonitrile, PVB, silicone, rubber, polyamide, synthetic rubber, vulcanized rubber, acrylic, polyethylene, polypropylene, polyethylene terephthalate, polytetrafluoroethylene, gore-tex, polycarbonate, etc.), a piezo electric device that can shape change with current introduction, shape memory polymers, magnetic shape memory alloys, temperature responsive polymers, pH-sensitive polymers, etc.). Without any limitation, suitable materials may include a cobalt-based low thermal expansion alloy referred to in the field as ELGELOY, nickel-based high temperature high-strength "superalloys" commercially available from Haynes International under the trade name HASTELLOY, nickel-based heat treatable alloys sold under the name INCOLOY by International Nickel, and a number of different grades of stainless steel. In some embodiments, materials retain a suitable amount of the deformation induced by a molding surface when subjected to a predetermined treatment. In some embodiments, a device comprises a shape memory alloy, NiTi (known as nitinol) which is an approximately stoichiometric alloy of nickel and titanium and may also include other minor amounts of other metals to achieve desired properties. Handling requirements and variations of NiTi alloy composition are known in the art. U.S. Pat. No. 5,067,489 (Lind) and U.S. Pat. No. 4,991,602 (Amplatz et al.), the teachings of which are incorporated herein by reference in their entireties, discuss the use of shape memory NiTi alloys. Such NiTi alloys are commercially available. NiTi alloys are also very elastic and are said to be "super elastic" or "pseudo elastic". This elasticity allows a device to return to a preset expanded configuration upon deployment.

In some embodiments, a device of the present invention is composed of material configured to block the flow of fluid (e.g. blood) except through designed channels (e.g. inner lumen, interior valve, axial aperture, etc.). In some embodiments, a device of the present invention is constructed of materials which are impermeable to blood, but the device contains a valve (e.g. one-way valve) within the lumen of the device which may allow blood to pass. In some embodiments, materials are selected for devices of the present invention which are not porous and/or do not allow fluid to pass through (e.g. polymers). In some embodiments, a device of the present invention in composed of or coated in impermeable materials. In some embodiments, a device of the present invention in composed of or coated in materials including but not limited to Bakelite, neoprene, nylon, PVC, polystyrene, polyacrylonitrile, PVB, silicone, rubber, polyamide, synthetic rubber, vulcanized rubber, acrylic, polyethylene, polypropylene, polyethylene terephthalate, polytetrafluoroethylene, gore-tex, polycarbonate, etc. In some embodiments, materials are selected to cover devices of the present invention which are not porous and/or do not allow blood to pass through. In some embodiments, devices of the present invention are composed of materials which are impermeable to fluids. In some embodiments, devices of the present invention are composed of materials which are non-permeable to fluids. In some embodiments, devices of the present invention are composed of materials which are impermeable to blood (e.g. polymer). In some embodiments, devices of the present invention are coated materials which are impermeable to blood (e.g. polymer). In some embodiments, devices of the present invention are coated materials which are non-permeable to blood. In some embodiments, a device of the present invention is comprised of a mesh or mesh-like weaving which is coated or covered in a material yielding a device which is impermeable to blood. In some embodiments, a device of the present invention is comprised of a mesh or mesh-like weaving which itself could allow blood to pass, but which is coated or covered in a material (e.g. polymer material) which makes the device impermeable to blood. In some embodiments, elements of a device of the present invention may be permeable to blood, but a region of a device of the present invention which surround or occlude the channel or opening in which the device is deployed are impermeable to blood. In some embodiments, the present invention provides a skeleton (e.g. exoskeleton, endoskeleton, etc.). In some embodiments, the present invention provides a skeleton (e.g. memory alloy skeleton, mesh skeleton, etc.) which is coated or covered in a blood-impermeable layer In some embodiments, the skeleton is configured to adopt a curvature or a shape such that it is able to conform to the inner, blood filled chamber of the heart (e.g. an umbrella-like or parabolic-like curve). In some embodiments, the present invention is configured to conform to the trabeculated inner surface of the heart. In some embodiments, the present invention is configured to conform to the outer anatomical shape of the heart. In some embodiments, the present invention is configured to conform to left ventricle apex, adopting a curvature that approximates the apex. In some embodiments, the inner and outer portions utilize an attachment to aid in shape conformation (e.g. suture, clip, anchoring mechanism). In some embodiments, attachment aids are placed along the outer circumference and/or interspersed radially at distance intervals from the center of the device to facilitate conformity and adherence to the inner and outer surfaces. In some embodiments, a skeleton provided by the present invention may comprise polymer, a cloth or material like a ptfe, goretex, etc, or other material that would provide for a physical barrier. In some embodiments a skeleton provided by the present invention may comprise a porous or mesh material coated or covered by polymer, a cloth or material like a ptfe, goretex, etc, or other material that would provide for a physical barrier. In some embodiments, the selected materials facilitate the prevention of bleeding leakage on deployment to act as a seal. In some embodiments, the present invention utilizes materials which aid in the formation of a seal in addition to, or instead of formation of clot and endothelialization to seal off compartments. In some embodiments, materials utilized in the present invention provide significantly quicker sealing as compared to normal clotting.

In some embodiments, a device of the present invention is configured to have an appropriate degree of flexibility and rigidity. In some embodiments, the device is configured to flex and move in concert with the heart's movement. In some embodiments, a device of the present invention may be rigid. In some embodiments, the flexibility of a device is adjustable or changes upon placement.

In some embodiments, the proximal and distal elements (e.g. expanded elements) are connected via a central element (e.g. cylinder unit). In some embodiments, the central element passes through the tissue of the heart. In some embodiments, the proximal and distal expanded elements sandwich the tissue from either end and provide a closure of that tissue. In some embodiments, minimal leakage (e.g. of blood, etc.) is capable of leaking around or through the device. In some embodiments, a device of the present invention maintains hemodynamic integrity and/or prevents hemodynamic compromise.

In some embodiments, a device of the present invention provides an axis point. In some embodiments, an axis point may be either one dimensional, two dimensional, or multi-dimensional at the point of interface (e.g. chest wall, skin, etc.) In some embodiments, an axis point facilitates stabilization of insertion and cannulization. In some embodiments, and axis point facilitates stabilization during the procedure of intervention into the heart while the heart continues to beat and oscillate. In some embodiments, an axis point provides flexibility in attachment allowing a device to move with the motion of the heart. In some embodiments, an axis point prevents dislodging of a device due to movement of the site of attachment.

In some embodiments, a device of the present invention may be of any suitable shape. In some embodiments, the shape of a device is selected based upon the location of insertion and the specific application. In some embodiments, a device of the present invention may have different shapes pre-insertion, during insertion, and following insertion. In some embodiments, shapes for a device of the present invention are selected from the list including but not limited to: disc, bell, bow tie, barbell, dumbbell, hour glass shaped, beads-on-a-string, nozzle, oval, cylindrical, circular, globular, spherical, flattened, derivations thereof, and combinations thereof.

In some embodiments, the present invention provides methods and devices for use in medical procedures and surgeries (e.g. cardiac surgery). In some embodiments, the present invention provides methods and devices for use in cardiac medical procedures and surgeries (e.g. angioplasty, percutaneous coronary interventions, laser angioplasty, atherectomy, stent procedure, bypass surgery, minimally invasive heart surgery, limited access coronary artery surgery, prot-access coronary artery bypass, minimally invasive coronary artery bypass graft, radiofrequency ablation, catheter ablation, heart valve replacement surgery, heart transplant, cardiomyoplasty, etc.). In some embodiments, the present invention provides methods and devices for use in cardiac medical procedures and surgeries which replace existing medical procedures and surgeries (e.g. angioplasty, percutaneous coronary interventions, laser angioplasty, atherectomy, stent procedure, bypass surgery, minimally invasive heart surgery, limited access coronary artery surgery, prot-access coronary artery bypass, minimally invasive coronary artery bypass graft, radiofrequency ablation, catheter ablation, heart valve replacement surgery, heart transplant, cardiomyoplasty, etc.). In some embodiments, the present invention facilitates minimally invasive and/or percutaneous access to one or more chambers of the heart and components thereof, or major great blood vessels and components thereof (e.g. right atrium, left atrium, coronary sinus, coronary arteries, pulmonary trunk, pulmonary arteries, right ventricle, left ventricle, left ventricular apex, aorta, the aortic arch, thoracic aorta, descending aorta, abdominal aorta, thoracoabdominal aorta, etc.). In some embodiments, a device of the present invention is used in performing a medical procedure or surgery. In some embodiments, a device of the present invention is used following a medical procedure or surgery.

In some embodiments, the present invention facilitates minimally invasive and/or percutaneous access to the left ventricular apex. In some embodiments, the present invention utilizes a percutaneous or minimally invasive pathway through a rib space, focusing directly to the apex of the heart, via a single access point through the skin. In some embodiments, the present invention provides multiple ports or points of access through multiple rib spaces or multiple points along the same rib space. In some embodiments, the present invention provides devices and methods for completion of a medical or surgical procedure through a single port or single access point through which a portion of a medical procedure or an entire procedure would be completed. In some embodiments, the procedure entails a small incision (e.g. <1 mm, <2 mm, <3 mm, <4 mm, <5 mm, <6 mm, <7 mm, <8 mm, <9 mm, <1 cm, <1.1 cm, <1.2 cm, <1.3 cm, <1.4 cm, <1.5 cm, <1.6 cm, <1.7 cm, <1.8 cm, <1.9 cm, <2 cm, <2.1 cm, <2.2 cm, <2.3 cm, <2.4 cm, <2.5 cm, <2.6 cm, <2.7 cm, <2.8 cm, <2.9 cm, <3.0 cm). In some embodiments, an incision is made prior to insertion and/or deployment of the device. In some embodiments, the incision is made as the device is inserted into the tissue. In some embodiments, the procedure entails placement of wires, dilators and other access tools into the heart (e.g. left ventricle apex). In some embodiments, use of the present invention in a procedure entails an incision of at least 1 mm (e.g. >1 mm, >2 mm, >3 mm, >4 mm, >5 mm, >6 mm, >7 mm, >8 mm, >9 mm, >1 cm, >1.1 cm, >1.2 cm, >1.3 cm, >1.4 cm, >1.5 cm, >1.6 cm, >1.7 cm, >1.8 cm, >1.9 cm, >2 cm, >2.1 cm, >2.2 cm, >2.3 cm, >2.4 cm, >2.5 cm, >2.6 cm, >2.7 cm, >2.8 cm, >2.9 cm). In some embodiments, a device of the present invention includes a valve that permits access for a variety of tools for placing the percutaneous valve, or carrying out other intra-cardiac procedures, but would prevent bleeding from the left ventricle because of a 1-way valve. In some embodiments, the invention is a closure device that would not require suture to be placed on the epicardium (surface, or outside) of the heart.

In some embodiments, a device of the present invention is placed in an opening (e.g. surgical incision) in a tissue (e.g. wall of the heart) of a subject (e.g. human patient). In some embodiments, the outer circumference of the cylinder element 11 approximates the size of the opening in the tissue (e.g. surgical incision). In some embodiments, the expanded elements of the present invention have maximum outer circumferences which are larger than the size of the opening in the tissue (e.g. surgical incision).

In some embodiments, a device of the present invention is placed in an incision in the heart. In some embodiments, a device of the present invention is placed in an incision in the heart and used as an entry port for the placement of medical tools, systems and devices (e.g. wires, leads, catheters, cameras, balloons, electrodes, surgical tools, delivery sheath, etc.). In some embodiments, a device of the present invention provides one or more inner apertures (e.g. inner lumen, axial aperture, etc.) for the insertion of medical tools, systems, and devices. In some embodiments, an inner lumen or aperture of the present invention is aligned axially along a cylinder element of the present invention. In some embodiments, an inner aperture of a device of the present invention is at least 0.1 mm (e.g. >0.1 mm, >0.2 mm, >0.3 mm, >0.4 mm, >0.5 mm, >0.6 mm, >0.7 mm, >0.8 mm, >0.9 mm, >1 mm, >2 mm, >3 mm, >4 mm, >5 mm, >6 mm, >7 mm, >8 mm, >9 mm, >1 cm, >1.1 cm, >1.2 cm, >1.3 cm, >1.4 cm, >1.5 cm, >1.6 cm, >1.7 cm, >1.8 cm, >1.9 cm, >2 cm, >2.1 cm, >2.2 cm, >2.3 cm, >2.4 cm, >2.5 cm, >2.6 cm, >2.7 cm, >2.8 cm, >2.9 cm, etc.). In some embodiments, an inner aperture of a device of the present invention is not greater than 2.9 cm (<2.9 cm, <2.8 cm, <2.7 cm, <2.6 cm, <2.5 cm, <2.4 cm, <2.3 cm, <2.2 cm, <2.1 cm, <2.0 cm, (<1.9 cm, <1.8 cm, <1.7 cm, <1.6 cm, <1.5 cm, <1.4 cm, <1.3 cm, <1.2 cm, <1.1 cm, <1.0 cm, etc.). In some embodiments, a device of the present invention provides an elongate tubular body with an axial lumen designed to provide s access to a diagnostic or treatment site in the body.

In some embodiments, a device of the present invention provides one or more medical tools, systems, and devices (e.g. wires, leads, catheters, cameras, balloons, electrodes, surgical tools, suction device, ablation device, etc.). In some embodiments, a device of the present invention provides one or more medical tools, systems, and devices as accessory elements to the present invention. In some embodiments, accessory elements of the present invention provide utility in placing the device of the present invention. In some embodiments, accessory elements provide utility in performing medical procedures and/or surgical procedures in conjunction with a device of the present invention. Systems and kits containing any one or more of these accessory components are provided as embodiments of the invention.

In some embodiments, medical and surgical devices are fed through one or more inner apertures of the present invention. In some embodiments, an inner aperture of the present invention provides an access point to an inner chamber of the heart or a major artery from outside the heart or artery. In some embodiments, a device of the present invention is configured to provide access to standard minimally invasive instruments. In some embodiments, a device of the present invention is configured to provide access to a set of minimally invasive instruments designed to perform optimally when inserted through a device of the present invention. In some embodiments, the relative length of devices inserted through the lumen of the present invention can be varied according to clinical need, as will be understood by those skilled in the art (e.g. 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 34 cm, 35 cm, 36 cm, 37 cm, 38 cm, 39 cm, 40 cm, >40 cm). In some embodiments, devices utilized in conjunction with the present invention can be manipulated from outside the heart (e.g. by a clinician or robot) to yield desired effects within the procedure area (e.g. heart (e.g. left ventricle)). In some embodiments, devices utilized in conjunction with the present invention are steerable. In some embodiments, control of inserted device or devices is provided by an integrated hand-held control mechanism and/or handle mounted on the proximal end of the devices. In some embodiments, the control mechanism/handle can be of various types, and adapted for operating steerable devices wherein a bend in the inserted device can be selectively controlled by the operator (e.g. clinician or robot). In some embodiments, the mechanism/handle includes a set of control switches, which allow the operator to control the steering of the inserted device and other operational functions. It will be apparent to one of ordinary skill in the art that other control mechanisms/handles can be employed with the systems of the invention without departing from the scope thereof. Specifically, other systems can include joystick controls for operating the inserted steerable devices and can include controls for rotating the angle at which the distal end of the devices bend. Other modifications and additions can be made to the control mechanism/handle without departing from the scope of the invention. In some embodiments, the control mechanism/handle also controls extension of an inserted device through the lumen of the present invention, steering of any devices inserted through the lumen, injection/ejection of any agents, electrical impulses, or any other functions that are understood by one in the art. In some embodiments, the aperture through a device of the present invention is configured to provide an environment for housing and/or delivering compositions (e.g. an imaging agent), systems, or devices (e.g. an electrophysiological device) to desired locations (e.g. major artery of chamber of the heart (e.g. left ventricle)). In some embodiments, the aperture through a device of the present invention may find utility in navigation, localization, mapping, or therapeutics within a desired work space (e.g. within a subject, animal, mammal, human, tissue, organ, the coronary sinus, etc.). In some embodiments the aperture through a device of the present invention is configured for injection of a composition (e.g. imaging agent (e.g. contrast agent)) and depositing the composition at a desired location (e.g. major artery of chamber of the heart (e.g. left ventricle)). In some embodiments, the lumen through the present invention is configured to deliver a liquid and/or solid composition to a desired site (e.g. major artery of chamber of the heart (e.g. left ventricle)). In some embodiments, the lumen is configured to house an electrophysiological device, which is capable of extending and retracting from the distal end of the lumen (e.g. into the heart). In some embodiments, the lumen is configured for multiple functions (e.g. housing an extendable electrode array, injection of a composition, restriction of blood flow).

In some embodiments, a device of the present invention adopts a collapsed conformation for insertion into an opening (e.g. surgical incision) in a tissue (e.g. coronary wall). In some embodiments, a expanded element 12, distal expanded element 12B, proximal expanded element 12A, proximal expanded element 22, and/or distal expanded element 32 of the present invention adopts a collapsed conformation for insertion into an opening (e.g. surgical incision) in a tissue (e.g. coronary wall). In some embodiments, a collapsed conformation is the result of pressure applied to insert a device of the present invention into a confining opening (e.g. surgical incision). In some embodiments, a device of the present invention is configured to adopt a collapsed conformation using a pre-insertion deformation process (e.g. pre-heating, pre-cooling, pre-pressurizing, physical manipulation, clamping, etc.). In some embodiments, a collapsed conformation is required for insertion. In some embodiments, a device of the present invention adopts an expanded conformation following insertion into an opening (e.g. surgical incision) in a tissue (e.g. coronary wall). In some embodiments, a device of the present invention adopts an expanded conformation following release of pressure upon the device. In some embodiments, a expanded element 12, distal expanded element 12B, proximal expanded element 12A, proximal expanded element 22, and/or distal expanded element 32 of the present invention adopts an expanded conformation following insertion into an opening (e.g. surgical incision) in a tissue (e.g. coronary wall). In some embodiments, an expanded conformation is adopted upon release of pressure applied to the device by a constrictive opening. In some embodiments, an expanded conformation is adopted upon release of a manipulative force (e.g. clamp, etc.) applied by an operator (e.g. clinician, surgeon, robot, etc.).

In some embodiments, a device is deployed (e.g. inserted, placed, etc.) into a channel or opening (e.g. incision) in a tissue of a subject through the use of a secondary device (e.g. catheter, forceps, tongs, etc.). In some embodiments, a catheter or other suitable delivery device may be positioned within a channel in a patient's body to place the distal end of the device adjacent the desired treatment site, such as immediately adjacent to or within the opening in the tissue of the subject. In some embodiments, the delivery device (e.g. catheter) can take any suitable shape, but may comprise an elongate flexible shaft. In some embodiments, a delivery device is used to urge the device through the lumen of a catheter for deployment in a channel (e.g. surgical incision) of a patient's body. In some embodiments, upon deployment of a device out the distal end of the delivery device (e.g. catheter), the device will still be retained by the delivery device. In some embodiments, once the device is properly positioned within the opening (e.g. surgical incision) in a tissue (e.g. coronary wall) of a subject, the device is released from the delivery means (e.g. the shaft of the delivery device can be rotated about its axis to unscrew the device from the delivery means). In some embodiments, by keeping the device attached to the delivery means, the operator can retract the device for repositioning relative to the opening, if it is determined that the device is not properly positioned within opening. In some embodiments, the operator can control the manner in which the device is deployed out the distal end of the catheter. In some embodiments, upon exiting the delivery device (e.g. catheter), a medical closure device will resiliently return to a preferred expanded shape and/or size. In some embodiments, upon deployment of a device out the distal end of the delivery device (e.g. catheter), the device is released from the delivery device.

In some embodiments, a device provides an expandable stabilizing instrument to stabilize the tissue structure within the heart chamber upon which the procedure is to be performed. In some embodiments, the expandable member comprises an inflatable balloon or expandable arms that engage the tissue surface to stabilize a device in the proper location for a given procedure.

In some embodiments, a device is used to temporarily or permanently occlude a channel (e.g. incision) in a patient's body. In some embodiments, a device is deployed in the patient's vascular system so that it may occlude a channel (e.g. incision) in a patient's body. In some circumstances, the medical device may be attached to a delivery system in such a manner as to secure the device to the end of the delivery means. Before removing the delivery means (e.g. catheter) in such a system, it may be necessary to detach the medical device from the delivery means before removing the delivery means (e.g. catheter).

In some embodiments, a device is configured to resiliently adopt its expanded configuration (e.g. its shape prior to being collapsed for passage through the catheter) upon deployment from a delivery device. In some embodiments, it is desirable that the device have a maximum outer diameter in its expanded configuration, at least as large or larger than the inner diameter of the lumen of the opening in which it is to be deployed.

In some embodiments, a device provides closure of an opening (e.g. surgical incision, defect, etc.) between one blood filled and/or pressurized compartment to a non blood filled compartment (e.g. a blood filled chamber of the heart to the outside of the heart, epicardial sack which is typically not filled with blood or fluid and if so in small quantities, or even a vessel such as a femoral artery or vein to the compartments outside the artery or vein, an air filled space or adjacent tissue or the arterial sheath, etc). In some embodiments, a device is deployed to close defects that are manmade, surgically produced, produced by an outside intervention, etc. as opposed to a congenital abnormality. In some embodiments a device is deployed to close congenital defects (e.g. to close a congenital hole in the outer wall of the heart or blood vessel).

EXPERIMENTAL

Example 1

Deployment of a Medical Closure Device of the Present Invention

The following example provides an exemplary deployment procedure for an exemplary medical closure device. This example should not be viewed as limiting, as deployment procedures, delivery components, and medical devices may differ from the example presented herein.

A medical closure device is placed into the lumen of a delivery catheter and positioned at the distal end of the catheter. The distal end of the medical closure device is positioned facing outward from the distal end of the delivery catheter. The confined space of the lumen of the delivery catheter compresses the distal and proximal expanded elements causing the expanded elements to adopt a reduced cross-sectional profile configuration.

Figure 4:
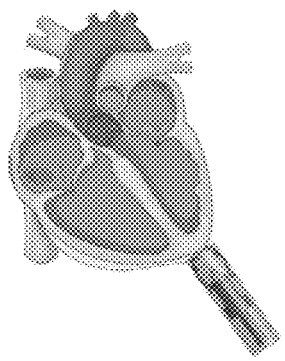
FIG. 4 shows a schematic of an exemplary device of the present invention being deployed into the left ventricular apex of a heart: (A) a delivery component properly aligns the device to the ventricular apex; (B) stabilization elements deploy to fix the delivery component in the proper position on the ventricular apex; (C) device is advanced in the ventricular apex; (D) distal expanded element takes a high profile configuration upon exiting the confined space of the delivery component and channel through the tissue; (E) following deployment, the delivery component is detached from the device and retracted.
Figure 4:
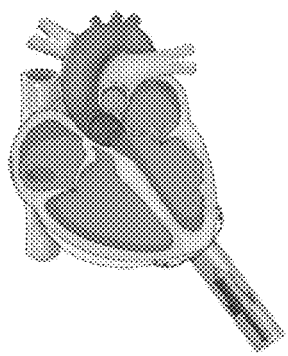
Figure 4:
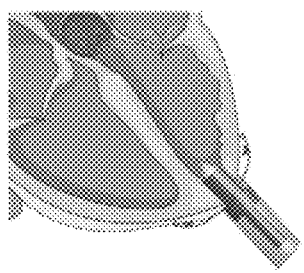
Figure 4:
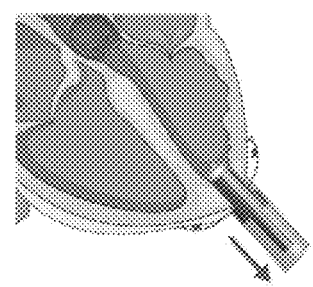
Figure 4:
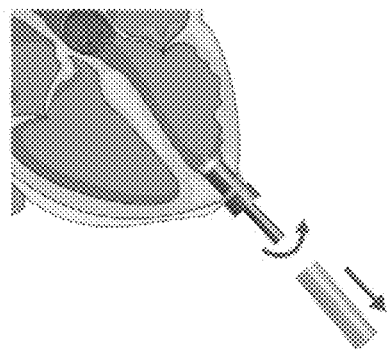

The delivery catheter is deployed via a minimally invasive pathway through a rib space directed toward the ventricular apex of the heart of a human patient (SEE FIG. 4A). The delivery catheter is positioned upon the ventricular apex. Adjustments to the position and angle of the delivery catheter are made to achieve optimal positioning over the procedure site. A pre-deployment surgical incision may have been made at the procedure site, or the device may be deployed to the site prior to any surgical incision. Once optimal positioning of the delivery catheter is achieved, stabilization elements are deployed to secure the position of the delivery catheter on the procedure site (SEE FIG. 4B).

The medical closure device is deployed from the distal end of the delivery catheter into the ventricular apex. The confined channel through which the device travels within the coronary tissue maintains the reduced cross-sectional profile configuration of the distal expanded element of the medical closure device (SEE FIG. 4C). Once the distal expanded element exits the channel through the apical tissue and enters the left ventricular space, the pressure on the distal expanded element is relieved allowing the element to readopt its pre-delivery expanded high profile cross-sectional profile (SEE FIG. 4D). The distal expanded element expands to form a seal against the inner ventricular apex. Upon successful deployment of the medical closure device, the delivery device is detached from the closure device. The delivery device is retracted from the coronary space. The distal end of the delivery catheter clears the proximal expanded element, allowing the element to readopt a high profile expanded cross-sectional profile (SEE FIG. 4E). The proximal expanded element expands to form a seal against the outer ventricular apex. The medical closure device is properly positioned within the ventricular apex to provide access, hemostasis, and closure of the incision/channel through the tissue.

Example 2

Access, Hemostasis, and Closure

The following example provides exemplary methods of use for an exemplary medical closure device. This example should not be viewed as limiting, as medical closure devices of the present invention find utility in a range of procedures and surgeries not detailed in the following example.

A medical closure device is deployed during a medical procedure to provide access to the procedure site. The device is deployed, as described in Example 1 for example, to the left ventricular apex of the heart of a patient. Upon insertion into the apical tissue, the device provides an access port for performing medical and surgical procedures within the left ventricular space. A one-way valve within the inner lumen of the medical closure device prevents the outflow of blood and fluid from the left ventricle or other heart chambers into the extra-cardiac space. The valve further provides access to the chambers of the heart for surgical and medical instruments. Instruments are also docked on the medical closure device to obviate the need for insertion through the device. A camera docked on the closure device assists in deploying the device and provides real-time images of the ventricular space, allowing clinicians to perform procedures, assess progress, and monitor the patient. An inflatable balloon device is inserted through the lumen of the closure device and is used to restrict blood flow to the coronary arteries when inflated, allow selective administration of cardioplegia, administer contrast or imaging agents, etc. The closure device provides access to ablation electrodes to allow ablation procedures to be performed with a high degree of accuracy. The closure device also provides ventricular access to surgical instruments for performing surgical procedures within the chambers of the heart. Additional instruments can be delivered through the medical closure device as needed for medical and surgical procedures.

The medical closure device provides an apical inner lumen and valve system through which hemostasis is regulated. The valve can be closed to completely occlude the escape of blood from the ventricular space into the extra-cardiac environment. Likewise, the valve system can be operated in one-way mode so as to restrict blood flow from the chambers of the heart, but to still provide access for medical and surgical instruments as described above. The distal and proximal expanded elements envelope the region surrounding the channel through the tissue occluding the flow of any blood which otherwise might leak around another device. The surfaces of the medical closure device provide a blood-impermeable skin, allowing the device to regulated blood flow and hemostasis while obviating the need to provide time for thrombus formation. The device provides real-time and immediate adjustment and regulation of blood flow and hemostasis.

The medical closure device provides multiple mechanisms for temporary or permanent closure of a channel through the apical cardiac tissue. (1) The device is inserted into the cardiac tissue with a pre-installed cap, attached by threading to the distal of proximal end of the medical closure device. The cap prevents blood flow through the inner lumen of the device. Removal of a distal or proximal cap can be performed using an accessory device inserted into the closure device from the extra-cardiac space. (2) The device is inserted into the cardiac tissue without an accessory closure mechanism. Using an external instrument, a plug is inserted into the inner lumen of the valve to provide closure. The plug is seated against the valve and can provide temporary or permanent closure of the port. (3) A medical closure device without an inner lumen is inserted into the cardiac tissue. This device offers a permanent closure option while reducing the complexity of the device and thereby the probability of any device failure. Additional mechanisms for closure are contemplated and devices of the present invention are not limited by any particular closure mechanism.

We claim:

1. A method for occluding blood flow through an incision in a coronary wall of a human heart comprising inserting into said incision a medical closure device comprising:
   a cylinder element;
   a proximal expanded element that extends circumferentially around the entire circumference of said cylinder element, wherein said proximal expanded element is configured to adopt a reduced profile configuration upon inserting said proximal expanded element into a confined space and to resiliently readopt a high profile configuration upon exit from said confined space; and
   a distal expanded element that extends circumferentially around the entire circumference of said cylinder element, wherein said distal expanded element is configured to adopt a reduced profile configuration upon inserting said distal expanded element into a confined space and to resiliently readopt a high profile configuration upon exit from said confined space;
   wherein when deployed through the incision in the coronary wall of a human heart said distal expanded element forms a seal against the inner surface of the coronary wall, said proximal expanded element forms a seal against the outer surface of the coronary wall, and said medical closure device occludes blood flow through the incision without the need for thrombus formation; and
   wherein said medical closure device comprises one or more lumens through said cylinder element that allow access through the incision from the exterior of the heart to the interior of the heart.

2. The method of claim 1, wherein the incision is within the coronary wall of the left ventricle.

3. The method of claim 2, wherein the incision is within the left ventricular apex.

4. The method of claim 3, wherein, when said medical closure device is deployed through the incision in the coronary wall of a human heart said distal expanded element forms a seal against the inner surface of the coronary wall that approximates an inner surface of the left ventricular apex and said proximal expanded element forms a seal against the outer surface of the coronary wall that approximates an outer surface of the left ventricular apex.

5. The method of claim 1, wherein at least one of said one or more lumens comprise a one-way valve.

6. The method of claim 1, wherein said medical closure device comprises a metal fabric skeleton.

7. The method of claim 6, wherein said metal fabric skeleton comprises one or more shape memory materials.

8. The method of claim 1, wherein said medical closure device comprises a blood-impermeable skin.

9. The method of claim 8, wherein said blood-impermeable skin comprises a polymer coating.

* * * * *